United States Patent [19]

Nepon

[11] Patent Number: 5,039,606

[45] Date of Patent: Aug. 13, 1991

[54] DIAGNOSTIC PROBE FOR DIABETES TYPE I PREDISPOSITION

[75] Inventor: Gerald T. Nepon, Bainbridge, Wash.

[73] Assignee: Virginia Mason Research Center, Seattle, Wash.

[21] Appl. No.: 114,559

[22] Filed: Oct. 29, 1987

[51] Int. Cl.$^5$ .................. C12Q 1/68; C07H 15/12
[52] U.S. Cl. ............................ 435/6; 536/27
[58] Field of Search ................ 435/6; 536/27

[56] References Cited

FOREIGN PATENT DOCUMENTS 8607464 12/1986 World Int. Prop. O. .

OTHER PUBLICATIONS

Kim, S. J., et al., "Identification of a Polymorphic Variant Associated with HLA-DQw3 . . .", Proc. Natl. Acad. Sci., vol. 82, pp. 8139-8143, 12/85.

Gregersen et al., "Molecular Diversity of HLA-DR4 Haplotypes", Proc. Natl. Acad. Sci., vol. 83, pp. 2642-2646, 4/86.

Nepom, B. S., et al., Specific HLA-DR4-Associated Histocompatibility Molecules Characterize Patients with Seropositive Juvenile Rheumatoid Arthritis, J. Clin. Invest., 74:287-291, 1984.

Holbeck, S. L., and G. T. Nepom, Exon-Specific Oligonucleotide Probes Localize HLA-DQβ Allelic Polymorphisms, Immunogenetics, 24:251-258, 1986.

Nepom, G. T., et al., Specific HLA Class II Variants Associated with IDDM, in The Immunology of Diabetes Mellitus, M. Jaworski et al., eds., Elsevier Science Publishers, pp. 9-20, 1986.

Nepom, G. T., et al., Identification of HLA-Dw14 Genes in DR4+ Rheumatoid Arthritis, The Lancet, ii:1002-1005, Nov. 1986.

Nepom, G. T., et al., The Molecular Basis for HLA Class II Associations with Rheumatoid Arthritis, J. Chin. Immunol., 7(1):1-7, 1987.

Schreuder, G. M., Th., et al., HLA-DQ Polymorphism Associated with Resistance to Type 1 Diabetes Detected with Monoclonal Antibodies, Isoelectric Point Differences, and Restriction Fragment Length Polymorphism, J. Exp. Med., 164:938-943, Sep. 1986.

Todd, J. A., et al., HLA-DQ2β Gene Contributes to Susceptibility and Resistance to Insulin-Dependent Diabetes Mellitus, Nature, 329:599-604, Oct. 15, 1987.

(List continued on next page.)

Primary Examiner—Robert A. Wax
Assistant Examiner—Frederick F. Tsung
Attorney, Agent, or Firm—Christensen, O'Connor, Johnson & Kindness

[57] ABSTRACT

An oligonucleotide probe for diagnosing predeposition or susceptibility to type I diabetes, capable of specifically hybridizing with the gene sequence

3'-GCGGGCRARGRGGGGRGCAG-5' or

5'-CGCCCGATACACCCCACGTC-3' wherein A is adenine, C is cytosine, G is guanine, T is thymine, and R is thymine or uracil. The probe may include at least 15 sequential nucleotides selected from the sequence

5'-GCCCGATACACCCCACGT-3' or

3'-CGGGCRARGRGGGGRGCA-5'

The probe may be labeled with a detectable marker, such as an enzyme or biotin, and may be supplied in a diagnostic kit in combination with: a substratum capable of absorbing DNA or cells, a restriction enzyme, and/or a detergent.

12 Claims, 4 Drawing Sheets

OTHER PUBLICATIONS

Michelsen, B., and A. Lernmark, Molecular Cloning of Polymorphic DNA Endonuclease Fragment Associates Insulin-Dependent Diabetes Mellitus with HLA-DQ, J. Clin. Invest., 79:1144–1152, Apr. 1987.

Nepom, B. S., et al., Specific Genomic Markers for the HLA-DQ Subregion Discriminate between DR4+ Insulin-Dependent Diabetes Mellitus and DR4+ Seropositive Juvenile Rheumatoid Arthritis, J. Exp. Med., 164:345–350, Jul. 1986.

Radka, S. F., et al., Molecular Complexity of HLA-DQw3: the TA10 Determinant is Located on a Subset of DQw3$\beta$ chains, Human Immunology, 18:287–300, 1987.

Kwok, W. W., et al., Mutational analysis of the HELA-DQ3.2 Insulin-Dependent Diabetes Mellitus Susceptibility Gene, *Proc. Natl. Acad. Sci. USA*, 86:1027–1030, Feb. 1989.

HLA CLASS II GENES ON CHROMOSOME 6

DIAGNOSTIC PROBE FOR DIABETES TYPE I PREDISPOSITION

TECHNICAL FIELD

This invention relates generally to genetic engineering and more particularly to DNA and RNA probes useful for diagnosing predisposition to disease states, specifically type I diabetes.

BACKGROUND OF THE INVENTION

Genetic screening for inherited diseases based on the use of specific gene probes is a promising technology that will augment both the breadth and the precision of genetic diagnostic testing. There are an estimated 3,000 genetic disorders known which result from a single gene mutation, for which the application of specific gene probes is of direct value. In addition, however, there are a number of common disorders, such as rheumatoid arthritis (RA) and type I diabetes (or insulin-dependent diabetes mellitus, IDDM, hereinafter "diabetes"), which result not from a single gene mutation but from a combination of genetic and possibly environmental factors. In such cases, genetic inheritance determines the predisposition, or disease risk, associated with a large proportion of clinical disease. Thus, genetic testing for diabetes should be viewed as the identification of genetic predisposition, distinct from the more conventional notion of a single gene defect resulting in a specific inherited disease.

The identification of a particular gene associated with predisposition to diabetes can be viewed from two different perspectives. On the one hand, the gene being detected may be linked on the chromosome to other genes which actually confer disease susceptibility, in which case the gene being tested would function as a marker gene. On the other hand, the gene being identified may itself contribute directly to disease, but only if other genetic elements or appropriate environmental agents are present. Both of these concepts are important for understanding the genetic predisposition to diabetes.

The major genetic contribution to both diabetes and rheumatoid arthritis is encoded in a portion of chromosome 6 known as the major histocompatibility complex. Within this gene complex, a series of 14 linked genes constitutes the HLA class II gene cluster. Products of these class II genes are essential in the normal immune response for the triggering of the activation steps which lead to immunity. Even when the immune system is activated inappropriately, and attacks normal tissue, causing autoimmunity, these class II molecules play an essential role in the immune activation which leads to disease. This has led to the concept that the role of the HLA class II genes in autoimmune diseases such as type I diabetes is to function as a permissive molecular signal, like a "green light" which signals the immune system to proceed with an attack on a particular target. In type I diabetes, the target is assumed to be cellular components associated with the insulin-secreting cells of the pancreas. Thus, in many respects, the question of genetic predisposition in diabetes is an issue of identifying which HLA class II genes are responsible for aberrant signals in the activation of the autoimmune response.

The association of HLA class II genes with diabetes and with rheumatoid arthritis has been suspected for some time. The products of HLA genes carry the HLA typing specificities, which are conventionally measured using serologic reactivities. These typing specificities are a partial measure of genetic polymorphisms within the HLA gene complex. One of these serologic polymorphisms, known as HLA DR4, is present in approximately 70-75% of patients with either type I diabetes or classic rheumatoid arthritis. The utility of this serologic marker for disease predisposition analysis is hampered, however, by the fact that approximately 35% of the normal population also type as HLA DR4.

SUMMARY OF THE INVENTION

In the research described below, specific gene probes were developed that distinguish not only among different class II genes in DR4 positive haplotypes, but also between several polymorphic alleles for several of these linked loci. Using these probes, the following discoveries were made: Different patterns of linked genes are present on different individuals who all type as HLA DR4. Different linked genes account for the susceptibility of DR4 individuals to type I diabetes compared to rheumatoid arthritis, even though they both "type" as HLA DR4. Notably, a specific polymorphic variant of one of these linked genes accounts for greater than 95% of the DR4-associated type I diabetes. Thus, specific gene probes based on individual gene sequences can be used for oligonucleotide typing to identify individuals having the polymorphic variant associated with genetic susceptibility to diabetes.

The invention provides such an oligonucleotide probe for diagnosing predisposition or susceptibility to type I diabetes in the form of an oligonucleotide capable of specifically hybridizing with the gene sequence

3'-GCGGGCRARGRGGGGRGCAG-5' or

5'-CGCCCGATACACCCCCACGTC-3' wherein A is adenine, C is cytosine, G is guanine, T is thymine, and R is thymine or uracil. The probe preferably includes at least 15 sequential nucleotides selected from the sequence

5'-GCCCGATACACCCCCACGT-3' or

3'-CGGGCRARGRGGGGRGCA-5'.

In the most preferred embodiment, the oligonucleotide probe includes at least

5'-CCGATACACCCCCAC-3' or

3'-GGCRARGRGGGGRG-5'.

The probe may be labeled with a detectable marker, such as an enzyme or biotin, and will typically be supplied in a diagnostic kit in combination with a substratum capable of adsorbing DNA or cells, a restriction enzyme, and/or a detergent.

BRIEF DESCRIPTION OF THE DRAWINGS

FIG. 1 depicts gene organization of the class II region of the HLA complex on human chromosome 6;

DETAILED DESCRIPTION OF THE PREFERRED EMBODIMENT

FIG. 1 illustrates the genes on chromosome 6 which constitute the HLA class II genetic complex. Several of these genes are highly polymorphic; that is, they exist in numerous allelic forms in the normal population. For instance, at least 50 alleles of the DRβ1 locus, and a dozen or so alleles of the DQα and DQβ loci are known to exist. In the FIGURE, asterisks mark genes known to be expressed: the DR and Dw allelic series, including Dw4(DR4) and Dw14(DR4) genes, representing alleles of the DRβ1 locus. The DQβ3.1(DQw3) and DQβ3.2(DQw3) genes represent alleles of the DQβ1 locus. Protein products of the genes marked with an asterisk have been identified on the surface of lymphoid cells where they participate in the activation events triggering the immune response. Thus, these genes encode the structural proteins used in the signaling events critical for the immune system activation in health and disease. The HLA DR4 specificity is carried by products of the DRβ1 locus. At least five different DRβ1 alleles all carry the HLA DR4 serologic specificity, and other alleles do not but instead carry HLA specificities known as DR1, DR2, etc.

Figure 2:
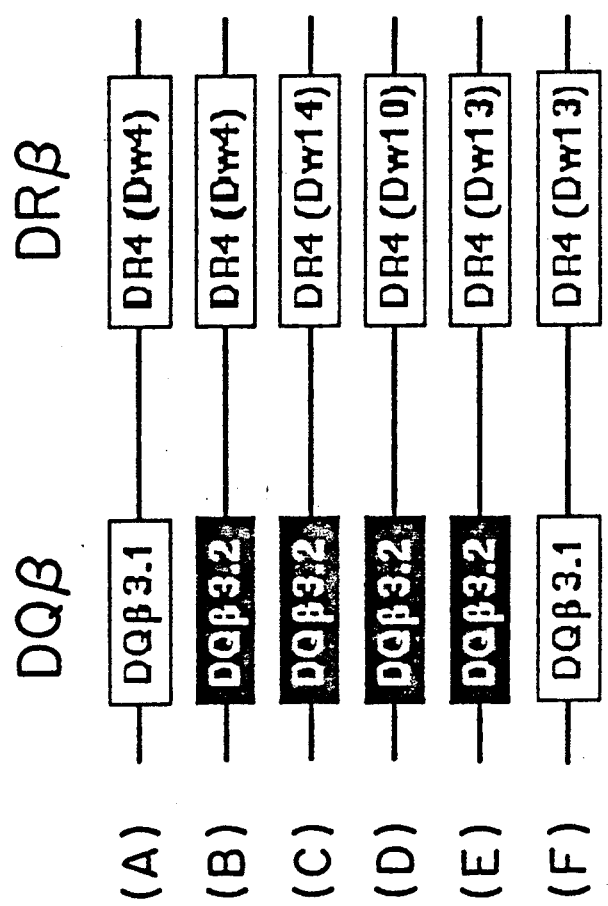
FIG. 2 diagrams the DR and DQ specificities associated with HLA-DR4, organized by haplotypes.

As shown in FIG. 2, each of the five alleles of DRβ1 genes on DR4 positive haplotypes have been given different names, such as Dw4, Dw14, Dw10, Dw13, Dw15. Each of these different DRβ1 alleles is linked to a polymorphic DQβ allele. The DQβ alleles are designated DQ3.1, DQ3.2, or DQx, as shown. An individual who "types" using conventional methodology as HLA DR4 potentially will carry any of the haplotypes illustrated in FIG. 2. In other words, up to five different alleles of DRβ and three different alleles of DQβ may be represented with the linkage patterns shown. In order to analyze the specific individual genes which account for the HLA DR4 association with type I diabetes, it was necessary to design techniques to distinguish among all these different DR and DQ alleles.

All of the different DR4 positive DRβ1 alleles are very closely related. They differ from each other by as few as one amino acid or as many as five amino acids. In keeping with this limited divergence, restriction enzyme recognition sites are conserved among these different alleles. In other words, restriction fragment linked polymorphisms (RFLP) do not distinguish among the different DR4 positive DRβ1 alleles.

Figure 3:
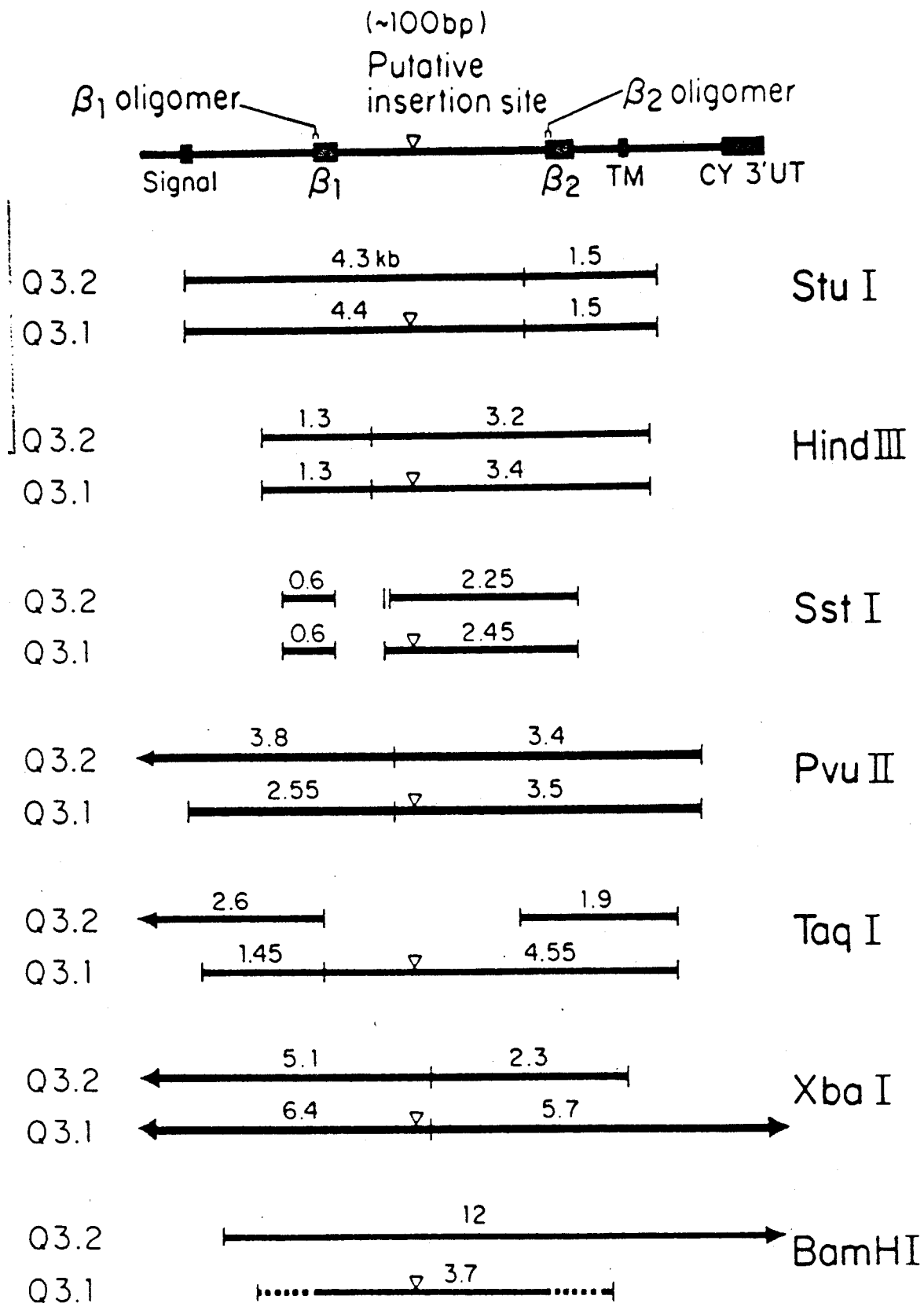
FIG. 3 depicts some restriction enzyme differences which distinguish the DQ3.1 and DQ3.2 alleles of the DQβ gene.

Referring to FIG. 2, three different alleles of the DQβ gene are found on DR4 positive haplotypes. These three alleles are fairly divergent from each other, and can be distinguished by either restriction enzyme polymorphisms (RFLP) or specific oligonucleotide probes. FIG. 3 highlights some of the restriction enzyme differences which distinguish the DQ3.1 and the DQ3.2 alleles. Analysis of type I diabetic patients and normal controls indicates that greater than 95% DR4 positive patients carry the DQ3.2 allele at the DQβ gene. This is the most highly associated HLA gene in this disease and apparently accounts for the association of the DR4 typing specificity noted previously. As illustrated in FIG. 2, the DQ3.2 gene is found linked to several different DRβ genes. In other words, the HLA class II gene most highly associated with DR4-positive diabetes is not the DRβ1 gene but the DQβ gene, and specifically its DQ3.2 allele.

In spite of the high association of the DQ3.2 allele with diabetes, it is important to emphasize that this gene, as with other HLA genes associated with autoimmune disease, predisposes the carrier toward, but is not solely responsible for, the inherited disease. This point is emphasized in FIG. 4, which shows that although the DQ3.2 gene accounts for most of the DR4 positive IDDM haplotypes, this gene is also present in a large number of unaffected individuals. These data confirm what had been observed in studies of identical twins: that diseases such as diabetes are not simple single-gene disorders. Multiple factors, possibly including more than one gene, and probably including some environmental interactions, presumably act in concert to lead to the full-blown disease syndrome. In this context, the particular predisposition gene plays some key permissive role, but is, by itself, not sufficient for disease expression. Nevertheless, identification of individuals having the DQ3.2 allele is of direct diagnostic value for assessing predisposition to type I diabetes.

The invention thus provides a gene probe useful for diagnosing predisposition to type I diabetes, in the form of an oligonucleotide capable of specifically hybridizing with the following distinguishing DQ3.2 gene sequence:

3'-GCGGGCTATGTGGGGGTGCAG-5'     (1)

or

5'-CGCCCGATACACCCCCACGTC-3'.    (2)

Since the DQ3.2 allele is expressed, e.g., in monocytes and B cells, RNA probes are also provided that are capable of specifically hybridizing with the following RNA sequence:

3'-GCGGGCUAUGUGGGGGUGCAG-5'.    (3)

By "specifically hybridizing" as used herein is meant that the subject probes are capable of hydridizing either with the sence or antisense strand of the DQ3.2 allele, or with RNA transcribed therefrom, at a stringency condition where a single base mismatch does not hybridize. Those skilled in the art will recognize that the stringency conditions for various hybridization assay formats will depend upon the constellation of temperature, ionic concentration, and pH. Generally, for optimal DNA:DNA or RNA:RNA hybridization, the temperature is inversely related to the salt concentration; the pH should be held, e.g., for 15-nucleotide sequences ("15-mers"), in the range of from about 6.8 to about 7.4. For RNA:DNA hybridizations, similar assay conditions apply, but lower temperatures (accompanied by higher salt concentrations) are generally employed than for the DNA:DNA hybridizations.

In other words, the subject probe should exactly complement all or part of oligonucleotide sequences (1), (2), or (3). Preferably, the bases complementary to terminal sequences of (1), (2), and (3) are not included in the probe construction, in order to increase the hybridization efficiency. Accordingly, the subject probes will generally contain sequential nucleotides selected from the following sequences:

5'-GCCCGATACACCCCCACGT-3'  (4)

or

3'-CGGGCTATGTGGGGGTGCA-5'  (5)

or

3'-CGGGCUAUGUGGGGGUGCA-5'.  (6)

The requisite specificity, with respect to the human genome, can be achieved by constructing the probe with any 15-nucleotide sequence from within (4), (5), or (6). Preferably, the probe should be such a 16-mer, which is considered to be optimal for commercial diagnostic applications at room temperature. For higher signal specificity, longer oligonucleotide sequences, including the 21-base sequences complementing (1), (2), or (3), can be selected, especially for clinical laboratory applications where auxiliary equipment for achieving higher hybridization temperatures is available.

For maximum efficiency, the probe contains a nucleotide sequence from the central region of (4), (5), or (6). Thus, in the most preferred embodiment, the subject probes will contain or include the following sequences:

5'-CCGATACACCCCCAC-3'  (7)

or

3'-GGCTATGTGGGGGTG-5'  (8)

or

3'-GGCUAUGUGGGGGUG-5'.  (9)

Such oligonucleotides can be readily synthesized by known techniques and available reagents and equipment. The subject probes can be detected or made detectable under various assay conditions in a number of conventional ways. For example, a radioisotope can be incorporated into the probe during oligonucleotide synthesis. Alternatively, an enzyme such as alkaline phosphatase can be conjugated to the probe prior to the assay, or a biotinylated probe can be employed in the assay and hybrids subsequently detected with an avidinized enzyme, e.g., streptavidin-alkaline phosphatase. Luciferins are also suitable for marking the oligonucleotide to make a probe, and the list of presently available detectable markers also includes fluorophores and other luminophores, enzyme inhibitors as well as coenzymes, paramagnetic metals and other spin labels.

The subject DNA and RNA probes can be employed in a wide variety of existing diagnostic hybridization assays, which generally include the steps of contacting patient-specific nucleic acids, either DNA or RNA or both, with an oligonucleotide probe capable of specifically hybridizing with a disease-associated polynucleotide sequence, and thereafter determining the presence or absence of the disease-associated DNA or RNA in the patient-specific sample by detecting DNA:DNA, RNA:RNA, DNA:RNA, or RNA:DNA hybrids formed between the probe and the patient-specific polynucleotides. In such assays, the hybridization can occur either on isolated nucleic acids or in situ, e.g., within patient-specific leukocytes, using available protocols in which the nuclear and/or plasma membranes of patient cells are permeabilized with detergents such as octoxynols (particularly Triton X-100) prior to incubation with the probe.

The subject probe will typically be supplied in diagnostic test kits in combination with one or more of the following reagents. A substratum capable of adsorbing or otherwise binding DNA and/or RNA will often be supplied with the probe. Available substrata for this purpose include membranes of nitrocellulose, nylon, or derivatized nylon that are generally characterized by bearing an array of positively charged substituents. One or more restriction enzymes, such as Taq I, may be furnished in the kit, as may nonhuman polynucleotides like calf-thymus or salmon-sperm DNA. For in situ hybridization, a detergent such as Triton X-100 may be supplied, along with a substratum, such as a transparent microscope slide, for binding the cells throughout the permeabilization, probe incubation and hybridization, and detection steps of the assay.

The invention is further illustrated by the following specific Example.

EXAMPLE

Patient selection and criteria: Type I diabetes (IDDM) patients were selected that fulfilled the criteria for juvenile onset insulin-dependent diabetes. Thirty-one caucasian DR4+ patients were available for this study. All of the DR4+ haplotypes were positive for HLA-DQw3. In five cases, the proband reported an IDDM affected sibling. DNA from all members of these five families was also obtained. Control DNA was obtained from 34 clinically normal DR4+ volunteers.

Preparation of genomic DNA: Peripheral blood leukocytes were washed 2× in Tris buffered saline, resuspended to $10^8$ cells per ml in TE [10 mM Tris, 1 mM ethylene diamine tetraacetate (EDTA), pH 7.6] and lysed with ten volumes of lysis buffer [10 mM Tris, pH 8.0, 2 mM EDTA, 10 mM NaCl, and 1% sodium dodecyl sulfate (SDS)] containing 200 μg/ml proteinase K for 18 hours at 37° C. After extraction with phenol:chloroform:isoamyl alcohol (25:24:1), ammonium acetate was added to a concentration of 2.0M, and DNA was precipitated by addition of absolute ethanol. Detailed procedures are provided in Holbeck, S. L., et al., *J. Immunol.* 135(1):637–641, 1985, hereby incorporated by reference.

Prior to gel electrophoresis, DNA was digested with restriction endonuclease Taq I (Bethesda Res. Labs.) at 2 u/μg DNA for four hours at 60°. Digested DNA was sorted by electrophoresis on 1% agarose gels, denatured and neutralized, then dried onto Whatman 3MM paper as described in Holbeck, S. L., and G. T. Nepom, *Immunogenetics* 24:251–258, 1986, and Nepom, G. T., et al., *The Lancet* ii(8514):1002–1005, 1986, both hereby incorporated by reference. Samples analyzed by slot blot hybridization (see below) were tested directly, without digestion or electrophoresis, after adsorption onto nitrocellulose paper.

Allele specific oligonucleotide probes and hybridization: Detailed procedures for the analysis of genomic DNA using allele-specific probes are described in Nepom et al., 1986, ibid. Briefly, gels or nitrocellulose slot blots containing digests of genomic DNA were hybridized for three hours at 55° in 6× NET (NaCl EDTA Tris), 10% dextran sulfate, 5× Denhardt's stock solution, 5 mM EDTA, 0.1% SDS, 0.05% NP-40 (Noniodet P-40), 250 μg/ml tRNA, and $10^7$ CPM/ml of the oligonucleotide probe, which was end-labeled with γ³²p-dATP and T4 polynucleotide kinase to give a specific activity of $10^9$ CMP/µg. Samples were washed with 5× SSC (sodium citrate stock solution), 0.5% SDS twice at room temperature for 10 min and twice at 55° for 30 min followed by washing with 3.2 mol tetramethylammonium chloride (TMACl) containing 0.5% SDS at 61° C., and then exposed to XAR-5 film for 1–7 days at −70° with Cronex Lightening Plus intensifying screens.

Probes DQβ3.1A25 and DQβ3.2A43 were synthesized, using an Applied Biosystems automated DNA synthesizer, by phosphoramidite analog chemistry as described by M. H. Carruthers in Methods of DNA and RNA Sequencing, pp 1–22, Weismann, S. M., e.d., Praeger Publishers, N.Y., 1983, hereby incorporated by reference. Their sequences were 5'-TCTGGTCACATAACGCACGCG-3' (DQβ3.1A25) and 5'-CGCCCGATACACCCCCACGTC-3' (DQβ3.2A43).

Characterization of probes for individual HLA-DQ genes: A DQβ gene probe that hybridizes to a conserved nucleotide sequence present in all DQβ genes is described in Holbeck and Nepom, 1986, supra. This probe identifies one gene per haplotype, the DQβ gene, and thus can be used to "HLA DQ type" genomic DNA analyzed by restriction enzyme digestions like those shown in FIG. 3. Results of such typing are illustrated in panel A of FIG. 2, in which genomic DNA from a variety of homozygous cells has been digested with the restriction enzyme Taq I, electrophoresed, and hybridized to the DQβ locus specific probe. Different alleles representing the DQw1, DQw2, DQ3.1, and DQ3.2 genes were distinguished by different sized fragments, corresponding to variation in the Taq I recognition sequences present on these different genes. The use of the allele specific oligonucleotide probe is illustrated in panel B of FIG. 2, wherein the same DNA blot for panel A was rehybridized with the DQ3.2 specific probe. Note that only the DQ3.2 genes were identified. The absence of a hybridization signal in genomic DNA from non-DQ3.2 haplotypes verified that the DQβ3.2A 43 probe is specific for a DNA sequence found only in the DQ3.2β gene.

Utilizing such allele specific probes, it became possible to rapidly analyze DNA for the presence or absence of individual DQβ genes. Panel C of FIG. 2 illustrates "slot-blot" hybridization analysis of a panel of DNA from different individuals, hybridized with the DQ3.1-specific oligonucleotide probe. In this procedure, genomic DNA prepared from peripheral blood leukocytes or cell lines was directly applied to nitrocellulose paper without digestion and without amplification. Radiolabeled probe DQ3.1A25 was then added, with hybridization indicating the presence of the specific DQβ3.1 gene. Slot-blot hybridization was also performed with the DQ3.2-specific probe.

DQ3.2 association with IDDM on multiple DR4+ haplotypes: DNA from thirty-one HLA-DR4 IDDM patients representing twenty-three unrelated sibships was analyzed with the DQ oligonucleotide probes; all thirty-one carried the DQ3.2 gene. Three individuals also carried the DQ3.1 gene; all three of these patients were homozygous for DR4, and heterozygous for DQ3.2 and DQ3.1.

As illustrated in FIG. 2, the DQ3.2 gene is present on several different DR4 positive haplotypes. In order to evaluate exactly which haplotypes were carried in the IDDM population, the linked DRβ alleles in each case were then analyzed. Allele-specific oligonucleotide probes distinguishing between different DR4+ DR genes, called Dw4, Dw14, and Dw10, were used for hybridization analysis of Eco RI digested genomic DNA, as described in Nepom et al., 1986, supra. Of the twenty-three separate unrelated DR4+ haplotypes in the IDDM population studied, seventeen (74%) carried a Dw4 gene (haplotype B in FIG. 2), four carried a Dw14 gene (haplotype C) and two carried other DRβ genes (D, E). In other words, several different DR4+ haplotypes were represented in the IDDM population, but all patients carried a DQ3.2 DQβ allele.

Figures 4, 5:
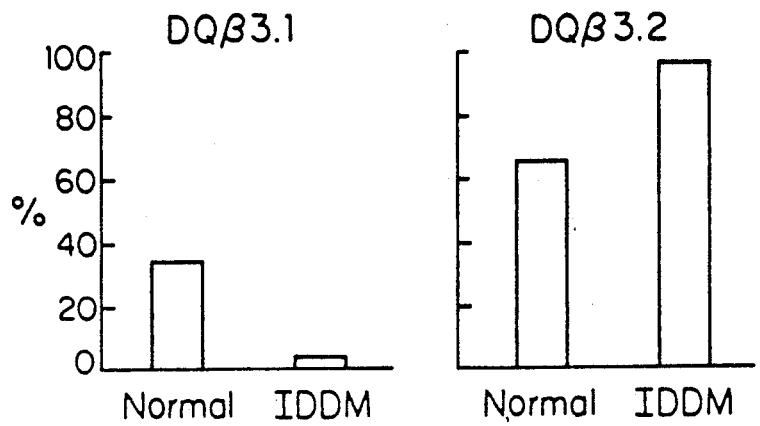
FIG. 4 compares distributions of the DQ3.1 and DQ3.2 alleles among normal and diabetic DRQ-positive individuals.
FIG. 5 summarizes the prevalence of DQ3.2 in type I diabetes patients versus controls.

Thirty-four nondiabetic DR4+ individuals were also analyzed using allelespecific DR and DQ DNA probes. DQ3.2 was present in 22 (65%), and DQ3.1 in 12 (35%). FIG. 5 summarizes the prevalence of DQ3.2 in patients versus controls, indicating the high sensitivity, but low specificity, of this gene marker among DR4 IDDM patients.

Haplotype A (FIG. 2) is a common DR4+ haplotype, with a DR gene identical to haplotype B, but differing at DQ. This haplotype carries a DQ3.1 allele and was found only in DR4-homozygous patients, when the patient's other haplotype carried a DQ3.2 gene. Because of this, and because the incidence of DQβ3.1 is lower in patients than in controls, haplotype A is considered a DR4+ haplotype that is not associated with IDDM. For susceptible DR4+ haplotypes associated with IDDM, the linked DRβ allele may vary, so long as the DQ3.2 gene is present.

Five families containing multiple affected IDDM siblings were also analyzed using the DNA probe methodology. In all five families, a DR4 positive haplotype segregated with IDDM. A total of thirteen affected siblings in the five families were analyzed; all 13 carried the DQ3.2 gene. Interestingly, in two of these families, the DQ3.2 gene was linked to a Dw4 gene (haplotype B), and in the other three families the DQ3.2 gene was linked to a Dw14 gene (haplotype C).

While the preferred embodiments of the invention have been illustrated and described, it is to be understood that, within the scope of the appended claims, various changes can be made therein. Hence, the invention can be practiced in ways other than those specifically described herein.

The embodiments of the invention in which an exclusive property or privilege is claimed are defined as follows:

1. A probe useful for detecting an allele associated with type 1 diabetes, consisting essentially of an oligonucliotide capable of specifically hybridizing with a gene sequence selected from the group consisting of:

3'-GCGGGCRARGRGGGGRGCAG-5', and

5'-CGCCCGATACACCCCCACGTC-3';

wherein
A is adenine,
C is cytosine,
G is guanine,
T is thymine, and
R is thymine or uracil.

2. The probe of claim 1, wherein the oligonucleotide consists essentially of about 16 nucleotides.

3. The probe of claim 1, wherein the oligonucleotide is labeled with a detectable marker.

4. The probe of claim 3, wherein the detectable marker is selected from among enzymes, biotin, radionuclides, fluorophores, luminophores, enzyme inhibitors, coenzymes, luciferins, paramagnetic metals and spin labels.

5. A diagnostic kit useful for diagnosing predisposition to type I diabetes, comprising a probe according to claim 1 in combination with a substratum capable of adsorbing DNA.

6. The diagnostic kit of claim 5, wherein the substratum comprises positively charged substituents.

7. A diagnostic kit useful for diagnosing predisposition to type I diabetes, comprising a probe according to claim 1 in combination with a restriction endonuclease.

8. The diagnostic kit of claim 7, wherein the restriction endonuclease is selected from the group consisting of Stu I, Hind III, Sst I, Pvu II, Taq I, Xba I, and BamH I.

9. The diagnostic kit of claim 7, wherein the restriction endonuclease is Taq I.

10. A diagnostic kit useful for diagnosing predisposition to type I diabetes, comprising a probe according to claim 1 in combination with a detergent for permeabilizing cell membranes.

11. The diagnostic kit of claim 10, wherein the detergent comprises an octoxynol.

12. In a method of genetic screening for inherited disease comprising the steps of contacting patient nucleic acids with a probe comprising an oligonucleotide capable of specifically hybridizing with a disease-associated polynucleotide sequence, and detecting the presence or absence of the disease-associated sequence in the patient nucleic acids, the improvement comprising contacting the patient nucleic acids with a probe according to claim 1.

* * * * *

UNITED STATES PATENT AND TRADEMARK OFFICE
CERTIFICATE OF CORRECTION

PATENT NO. : 5,039,606
DATED : August 13, 1991
INVENTOR(S) : G.T. Nepom It is certified that error appears in the above-identified patent and that said Letters Patent is hereby corrected as shown below:

| COLUMN | LINE | ERROR |
|---|---|---|
| [75] | 1 | "Gerald T. Nepon" should be --Gerald T. Nepom-- |
| [57] | 2 | "predeposition" should be --predisposition-- |
| [57] | 5 | "3'-GCGGGCRARGRGGGGRGCAG-5'" should be --3'-GCGGGCRARGRGGGGGRGCAG-5'-- |
| [57] | 7 | "5'-CGCCCGATACACCCCACGTC-3' should be --5'-CGCCCGATACACCCCACGTC-3'-- |
| [57] | 18 | "absorbing" should be --adsorbing-- |
| 7 | 2 | "CMP/$\mu$g" should be --CPM/$\mu$g-- |
| 7 | 41 and 42 | "DQ$\beta$3.2A 43" should be --DQ$\beta$3.2A43-- |
| 8 | 14 | "allelespecific" should be --allele-specific-- |

Signed and Sealed this

Sixth Day of April, 1993

*Attest:*

STEPHEN G. KUNIN

*Attesting Officer*       *Acting Commissioner of Patents and Trademarks*